(12) United States Patent
Muraki et al.

(10) Patent No.: US 8,213,009 B2
(45) Date of Patent: Jul. 3, 2012

(54) MICROPARTICLES MEASURING APPARATUS

(75) Inventors: Yosuke Muraki, Tokyo (JP); Masaya Kakuta, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 12/780,376

(22) Filed: May 14, 2010

(65) Prior Publication Data

US 2011/0069310 A1    Mar. 24, 2011

(30) Foreign Application Priority Data

May 21, 2009  (JP) ................................ P2009-123039

(51) Int. Cl.
*G01N 15/02* (2006.01)
(52) U.S. Cl. ....................................... 356/335; 356/336
(58) Field of Classification Search .......... 356/335–339, 356/72, 39; 250/458.1–461.2; 340/539.1–539.29, 340/870.01–870.17
See application file for complete search history.

(56) References Cited

U.S. PATENT DOCUMENTS

| | | | | |
|---|---|---|---|---|
| 4,940,326 A | * | 7/1990 | Tatsuno | ........................ 356/336 |
| 7,439,855 B1 | * | 10/2008 | Yufa | ........................... 340/539.1 |
| 2007/0188737 A1 | * | 8/2007 | Fritz | ............................... 356/39 |

FOREIGN PATENT DOCUMENTS

| | | |
|---|---|---|
| JP | 2003-107099 | 4/2003 |
| JP | 2007-46947 | 2/2007 |

* cited by examiner

*Primary Examiner* — Tri T Ton
(74) *Attorney, Agent, or Firm* — K&L Gates LLP

(57) ABSTRACT

Disclosed herein is a microparticles measuring apparatus including: an optical detecting section configured to direct a laser beam toward microparticles passing through a flow channel, detect light emanating from the microparticles, and convert the detected light into electrical signals; and a controlling unit configured to calculate the speed of the microparticles passing through the flow channel according to the electrical signals and suspend the supply of solution containing the microparticles when the calculated speed exceeds a prescribed limit.

6 Claims, 4 Drawing Sheets

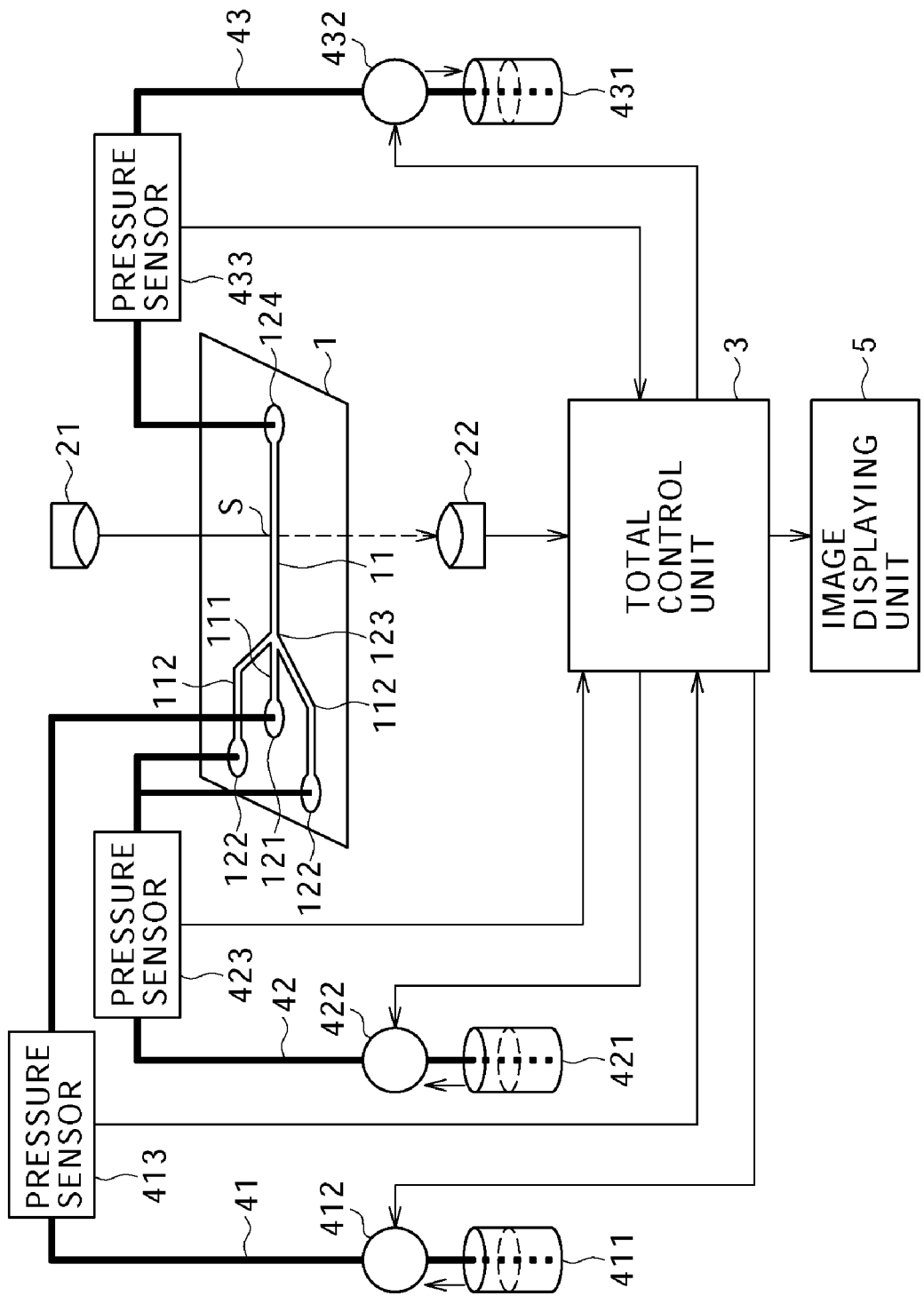

MICROPARTICLES MEASURING APPARATUS

CROSS REFERENCES TO RELATED APPLICATIONS

The present application claims priority to Japanese Priority Patent Application JP 2009-123039 filed in the Japan Patent Office on May 21, 2009, the entire content of which is hereby incorporated by reference.

BACKGROUND

The present application relates to a microparticles measuring apparatus and, more particularly, to a microparticles measuring apparatus which detects a leakage of sample solution and sheath solution and thereby suspends the operation automatically.

There has been an apparatus used to optically identify the characteristic properties of such microparticles as those associated with living bodies (e.g., cells, microorganism, liposomes) and any synthetic microparticles for industrial use, such as latex particles and gel particles. It is so designed as to introduce a dispersion of microparticles into a flow channel and direct a light beam to the microparticles passing through the flow channel.

Most popular among apparatuses to measure microparticles associated with living bodies is a flow cytometry, which is called a flow cytometer. (See "Saibou Kougaku (Cell Engineering), supplement volume, Experiment Protocol Series, Mastering of Flow Cytometry," by H. Nakauchi, issued by Shuujunsha, 2nd edition, issued Aug. 31, 2006, referred to as Non-Patent Document 1 hereinafter.) One type of it is intended only to identify the characteristic properties of microparticles and the other is designed to fractionate microparticles with desired properties according to the results of measurement obtained by the first type. The latter which is used to fractionate cells is referred to as "cell sorter."

The flow cytometery in the related art is so designed as to determine the characteristic properties (e.g., size and structure) of such microparticles as cells and microbeads in the following manner. A sample solution containing microparticles of interest is introduced into the center of the laminar flow of a sheath solution passing through a flow cell, so that the microparticles are lined up in the flow cell. The microparticles passing in a line through the flow cell is illuminated with a light beam, and the scattered light or fluorescent light emanating from them is detected for determination of their characteristic properties. This step may optionally be followed by fractionation of microparticles having desired characteristic properties in such a way that the sample solution containing microparticles is discharged in the form of droplets from the flow cell and individual droplets are moved in different controlled directions.

Japanese Patent Laid-Open No. 2007-46947 (referred to as Patent Documents 1 hereinafter) discloses a cell sorter in the related art (as shown in its FIG. 7) which is composed of a flow cell having a flow channel that causes cells (dyed with a fluorescent labeling reagent) to be lined up therein, an optical system that illuminates the cells with a laser beam and detects scattered light or fluorescent light, and a cell fractionating system that controls the moving direction of droplets discharged out of the flow cell.

In the meantime, there has recently been developed a microchip which is composed of a silicon or glass substrate and a region or flow channel formed thereon to perform chemical or biological analysis. The analytical system using such a microchip is referred to as μ-TAS (micro-total-analysis system) or labo-on-chip or biochip.

The μ-TAS may be applied to the technology for fractionation of microparticles which examines microparticles for their characteristic properties in optical, electrical, or magnetic ways while they are passing through the flow channel or region formed on the microchip. An example of the microchip for separation of microparticles is disclosed in Japanese Patent Laid-Open No. 2003-107099 (referred to as Patent Document 2 hereinafter). It is composed of a first flow channel into which is introduced a solution containing microparticles, a second flow channel for sheath solution arranged along at least one side of said first flow channel (both flow channels being formed on the same substrate), a microparticle measuring unit for passing through said first flow channel, and at least two flow channels (placed downstream the measuring unit) for separation and collection of microparticles. The foregoing microchip has electrodes near the transitional part between the measuring unit and the separating flow channel. The microparticle fractionating apparatus based on the microchip controls the moving direction of microparticles by means of their reaction to the electric field of the electrodes, so that it can perform fractionation of microparticles.

The flow cytometery (of microchip type) based on μ-TAS may have the flow channel formed on a disposable microchip so as to prevent cross-contamination of samples during measurement. However, this advantage is offset by the following disadvantage arising from the vulnerability of the microchip and parts in the measuring unit connected thereto. That is, the microchip itself and the connection between the microchip and the measuring unit get fatigued and break after prolonged use, which leads to a leakage of sample solution and sheath solution. This trouble also occurs when the connection between the microchip and the measuring unit cracks under stresses after repeated replacement of microchips.

SUMMARY

As mentioned above, the flow cytometery of microchip type is subject to a leakage of sample solution and sheath solution because of the vulnerability of the microchip and the measuring unit connected thereto. This leakage causes the measuring unit to malfunction or break; therefore, it should be detected immediately so as to suspend operation and replace the malfunctioning microchip and connection. Unfortunately, this is difficult to achieve for the flow cytometery of microchip type which needs frequent replacement of microchips and hence put difficulties in arranging sensors around the microchip and in detecting solution leakage by means of sensors.

It is desirable to provide a new flow cytometery which detects a leakage of sample solution and sheath solution and automatically suspends the supply of solutions without arranging sensors around the microchip, according to an embodiment.

The present application to achieve the foregoing desire in an embodiment covers a microparticles measuring apparatus which includes optical detecting means for directing a laser beam toward microparticles passing through a flow channel, detecting light emanating from the microparticles, and converting the detected light into electrical signals, and controlling means for calculating the speed of the microparticles passing through the flow channel according to the electrical signals and suspending the supply of solution containing the microparticles when the calculated speed exceeds a prescribed limit.

In the microparticles measuring apparatus, the controlling means calculates the speed based on the fact that the speed is inversely proportional to the pulse width of the electrical signals.

To be specific, the microparticles measuring apparatus includes a flow channel formed on a microchip, supplying means for introducing into the flow channel a sample solution containing microparticles and/or a sheath solution, discharging means for discharging the sample solution and/or the sheath solution from the flow channel, optical detecting means for directing a laser beam toward microparticles passing through the flow channel, detecting light emanating from the microparticles, and converting the detected light into electrical signals, and controlling means for calculating the speed of the microparticles passing through the flow channel according to the electrical signals and suspending the action of the supplying means when the calculated speed exceeds a prescribed limit.

In the microparticles measuring apparatus, the supplying means and the discharging means should preferably be equipped with a sensor to detect the flow rate of the sample solution and/or the sheath solution. In addition, the microparticles measuring apparatus should preferably have image displaying means for displaying the sensor which has detected the flow rate exceeding a prescribed limit. The microparticles measuring apparatus should preferably be constructed such that it suspends the action of the supplying means when the speed of microparticles passing through the flow channel exceeds a prescribed limit and it displays any one of the sensors which has detected the flow rate exceeding a prescribed limit on the image displaying means.

The term "microparticles" as used in the present application embraces any microparticles associated with living bodies, such as cells, microorganisms, and liposomes, and any synthetic microparticles for industrial use, such as latex particles and gel particles.

Microparticles associated with living bodies include chromosomes in various cells, liposomes, mitochondria, and organelles. The cells include animal cells (such as blood cells) and vegetable cells. The microorganisms include bacteria such as *Escherichia coli*, viruses such as tobacco mosaic virus, and fungi such as yeast. They also include polymers such as nucleic acids, proteins, and complexes thereof. Microparticles for industrial use include those of organic or inorganic polymeric material and metallic material. The organic material includes polystyrene, styrene-divinylbenzene, and polymethyl methacrylate. The inorganic polymeric material includes glass, silica, and ceramics. The metallic material includes gold colloid and aluminum. These microparticles are usually spherical but may be aspherical in some cases. They are not specifically restricted in size and mass.

According to an embodiment, there is provided a new flow cytometery which detects a leakage of sample solution and sheath solution and automatically suspends their supply without the necessity of arranging sensors around the microchip.

Additional features and advantages are described herein, and will be apparent from the following Detailed Description and the figures.

BRIEF DESCRIPTION OF THE FIGURES

FIG. 1 is a schematic diagram illustrating the configuration of the microparticles measuring apparatus according to an embodiment;

DETAILED DESCRIPTION

Figure 2A:
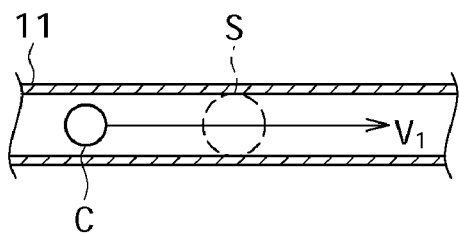
FIGS. 2A to 2D are schematic diagrams illustrating how the total control unit calculates the speed of microparticles passing through the flow channel.

The present application will be described below with reference to the accompanying drawings according to an embodiment. The description is divided into sections listed below.

1. Configuration of the microparticles measuring apparatus
(1) Microchip
(2) Optical detecting section
(3) Supplying section and discharging section
(4) Total control unit
2. Action of the microparticles measuring apparatus
1. Configuration of the Microparticles Measuring Apparatus FIG. 1 is a schematic diagram illustrating the configuration of the microparticles measuring apparatus A according to the present embodiment.

(1) Microchip

In FIG. 1, the microchip is indicated by a reference number 1. The microchip 1 has a flow channel 11 formed thereon which permits a sample solution (containing microparticles to be measured) to flow therethrough. The flow channel 11 also permits microparticles passing therethrough to be examined for optical properties. The flow channel 11 has a branched flow channel 111 into which the sample solution is introduced through the sample solution inlet 121. It also has branched flow channels 112 and 112 into which the sheath solution is introduced through the sheath solution inlets 122 and 122. The sample solution and the sheath solution join together at the junction 123 in such a way that the sample solution in laminar flow (which has been introduced through the branched flow channel 111) is held between the sheath solution in laminar flow (which has been introduced through the sheath solution inlets 122 and 122). Thus, microparticles in the sample solution are lined up in its laminar flow while they pass through the flow channel 11.

The microchip 1 is formed from glass or various plastics (such as PP (polypropylene), PC (polycarbonate), COP (cycloolefin copolymer), and PDM (polydimethylsiloxane)). A suitable material should be selected which is transparent to the illuminating light from the optical detecting sections 21 and 22 (mentioned later), has a low level of self fluorescence emission, and has a low level of wavelength dispersion (which is desirable for limited optical errors).

The flow channel 11 etc. on the microchip 1 may be formed by performing wet etching or dry etching on a glass substrate. They may also be formed by nanoimprinting on a plastic substrate or by injection molding and machining. The microchip 1 may be formed by sealing the substrate (on which the flow channel 11 etc. have been formed) with any material which is identical with or different from the substrate.

(2) Optical Detecting Section

The microparticles passing through the flow channel 11 are examined for optical properties by the paired optical detecting sections 21 and 22. The optical detecting section 21 directs a laser beam toward the microparticles and the optical detecting section 22 receives light emanating from the microparticles and converts the received light into electrical signals. That part of the microchip to which the laser beam is directed from the optical detecting section 21 will be referred to as "illuminating part S" hereinafter. Incidentally, the flow channels for sample solution and sheath solution in the microparticles measuring apparatus A are not restricted to those mentioned above so long as they are capable of allowing microparticles to line up in the laminar flow of the sample solution and feeding the sample solution to the illuminating part S.

The optical detecting sections 21 and 22 may have the same structure as those in the flow cytometery in the related art. To be specific, the optical detecting section 21 is an illuminator composed of a laser light source, a condenser lens to direct the laser beam to microparticles, a dichroic mirror, and a band-pass filter. The optical detecting section 22 is a detector to detect light emanating from microparticles illuminated by the laser beam. The detector is composed of a PMT (photomultiplier tube) or an area imaging device such as CCD and CMOS elements. Incidentally, the illustrated one is composed of separate illuminating and detecting systems. However, they may be combined into one system.

The light detecting sections 21 and 22 detect light emanating from the microparticles being illuminated by the laser beam. The light for detection may be fluorescent light or scattered light due to forward scattering, side scattering, Rayleigh scattering, and Mie scattering. The detected light is subsequently converted into electrical signals to be sent to the total control unit 3. Using the electrical signals, the total control unit 3 determines the characteristic properties of the microparticles and calculates the flow rate of the microparticles passing through the flow channel 11.

Incidentally, the optical detecting sections 21 and 22 in the microparticles measuring apparatus A may be replaced by electrical or magnetic detecting sections. In this case, the flow channel 11 is flanked with minute electrodes facing each other which measure changes in resistance, capacitance, inductance, impedance, electric field, magnetic field, or magnetization between them.

(3) Supplying Section and Discharging Section

There are shown in FIG. 1 the sample solution feeding section 41 which introduces the sample solution into the sample solution inlet 121, the sample solution reservoir 411 to store the sample solution, the sheath solution feeding section 42 which introduces the sheath solution into the sheath solution inlets 122 and 122, and the sheath solution reservoir 421 to store the sheath solution. The sample solution feeding sections 41 and the sheath solution feeding section 42 have feeding pumps of ordinary type and the valves 412 and 422 which start and stop the feeding of the sample solution and the sheath solution. The total control unit 3 outputs signals to the valves 412 and 422 to control the opening and closing thereof.

The sample solution feeding section 41 is provided with the sensor 413 to detect the flow rate of the sample solution being supplied from the sample solution reservoir 411. The sensor 413 is interposed between the sample solution inlet 121 and the valve 412 so that it detects the flow rate of the sample solution passing through it and sends the detected flow rate to the total control unit 3. Likewise, the sheath solution feeding section 42 is also provided with the sensor 423 to detect the flow rate of the sheath solution being supplied from the sheath solution reservoir 421. The sensor 423 is interposed between the sheath solution inlet 122 and the valve 422 so that it detects the flow rate of the sheath solution passing through it and sends the detected flow rate to the total control unit 3.

The sample solution and the sheath solution, which have entered the flow channel 11 and passed through the illuminating part S, is discharged out of the microchip 1 through the outlet 124 by the discharging section 43 and then introduced into the waste liquid tank 431. The discharging section 43 is provided with the sensor 433, which is interposed between the outlet 124 and the valve 432. The sensor 433 detects the flow rate of the sample solution and the sheath solution passing through it and sends the detected flow rate to the total control unit 3. The discharging section 43 has a feeding pump of ordinary type and the valve 432 which starts and stops the feeding of the sample solution and the sheath solution in response to signals from the total control unit 3.

The sensors 413, 423, and 433 in the microparticles measuring apparatus A may be any of flow rate sensor, pressure sensor, bubble detecting sensor, conductivity sensor, electrochemical sensor, differential refractometer, fluorescence detector, and UV-VIS detector, so long as they are capable of detecting the flow rate (or pressure) of the sample solution or sheath solution. Incidentally, the sensors shown in FIG. 1 are pressure sensors.

(4) Total Control Unit

The total control unit 3 receives electric signals from the optical detecting sections 21 and 22 and judges the optical properties of the microparticles according to the received signals. Parameters for judgment depend on the microparticles to be measured and the object of measurement; they include electrical signals converted from forward scattered light (for size determination), side scattered light, Rayleigh scattered light, or Mie scattered light (for structure determination), and fluorescence. The parameters are analyzed in the same way as in the flow cytometry in the related art. Parameters used to electrically or magnetically detect the characteristic properties of microparticles may be electrical signals converted from changes in resistance, capacitance, inductance, impedance, electric field, magnetic field, or magnetization.

The total control unit 3 also receives electrical signals from the optical detecting sections 21 and 22 and calculates the speed of microparticles passing though the flow channel 11 according to the received signals. When it finds that the calculated speed is outside the prescribed range, it sends signals to the sample solution feeding section 41 and the sheath solution feeding section 42 to suspend their action. In other words, when the flow rate of microparticles passing through the flow channel 11 becomes higher or lower than the prescribed value, the total control unit 3 sends signals to close the valves 412 and 422 so that the sample solution feeding section 41 and the sheath solution feeding section 42 suspend the supply of the sample solution and the sheath solution. As a consequence, the flow of microparticles in the apparatus completely stops.

As mentioned above, the total control unit 3 is informed of the flow rate of the sample solution and/or sheath solution detected by the sensors 413, 423, and 433, and suspends the action of the sample solution feeding section 41 and the sheath solution feeding section 42 in response to the thus received information. In this case, it causes the image displaying unit 5 to display the sensor which has detected the flow rate outside the prescribed range.

FIG. 2 shows how the total control unit 3 calculates the flow rate of microparticles passing through the flow channel 11. FIG. 2A is a schematic diagram showing a microparticle C passing at a flow rate V1 through the flow channel 11. FIG. 2B is a schematic diagram showing an electrical signal obtained by conversion of light emanating from the microparticle C. FIG. 2C is a schematic diagram showing a microparticle C passing at a flow rate V2 (V1>V2) through the flow channel 11. FIG. 2D is a schematic diagram showing an electrical signal obtained by conversion of light emanating from the microparticle C. In FIGS. 2A and 2C, the illuminating part S coincides with the spot of the laser beam directed from the optical detecting section 21. In FIGS. 2B and 2D, the abscissa represents time and the ordinate represents signal intensity.

Figure 2B:
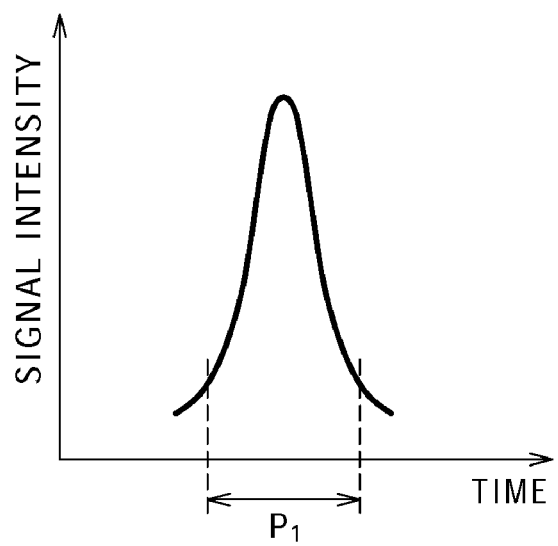
Figure 2C:
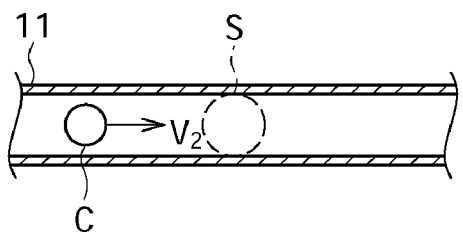
Figure 2D:
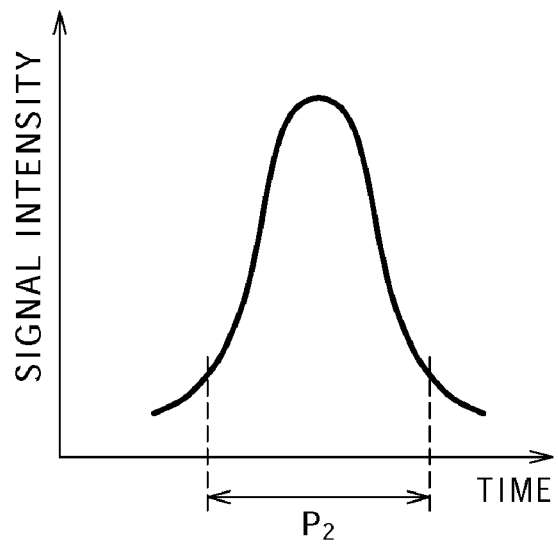

The microparticle C passing at a flow rate V1 through the flow channel 11 as shown in FIG. 2A emanates light when it crosses the illuminating part S, and this light is converted into an electrical signal which has a pulse width P1 as shown in FIG. 2B. In contrast, the microparticle C passing at a flow rate V2 through the flow channel 11 as shown in FIG. 2C emanates light when it crosses the illuminating part S, and this light is converted into an electrical signal which has a pulse width P2 as shown in FIG. 2D. The pulse width P1 is smaller than the pulse width P2. This means that the speed of the microparticle C passing through the flow channel 11 is inversely proportional to the pulse width P of the electrical signal obtained by conversion of light emanating from the microparticle. The pulse width of the electrical signal produced by the detecting system of the optical detecting sections 21 and 22 is utilized by the total control unit 3 to calculate the speed of the microparticle passing through the flow channel 11.

2. Action of the Microparticles Measuring Apparatus

Figure 3:
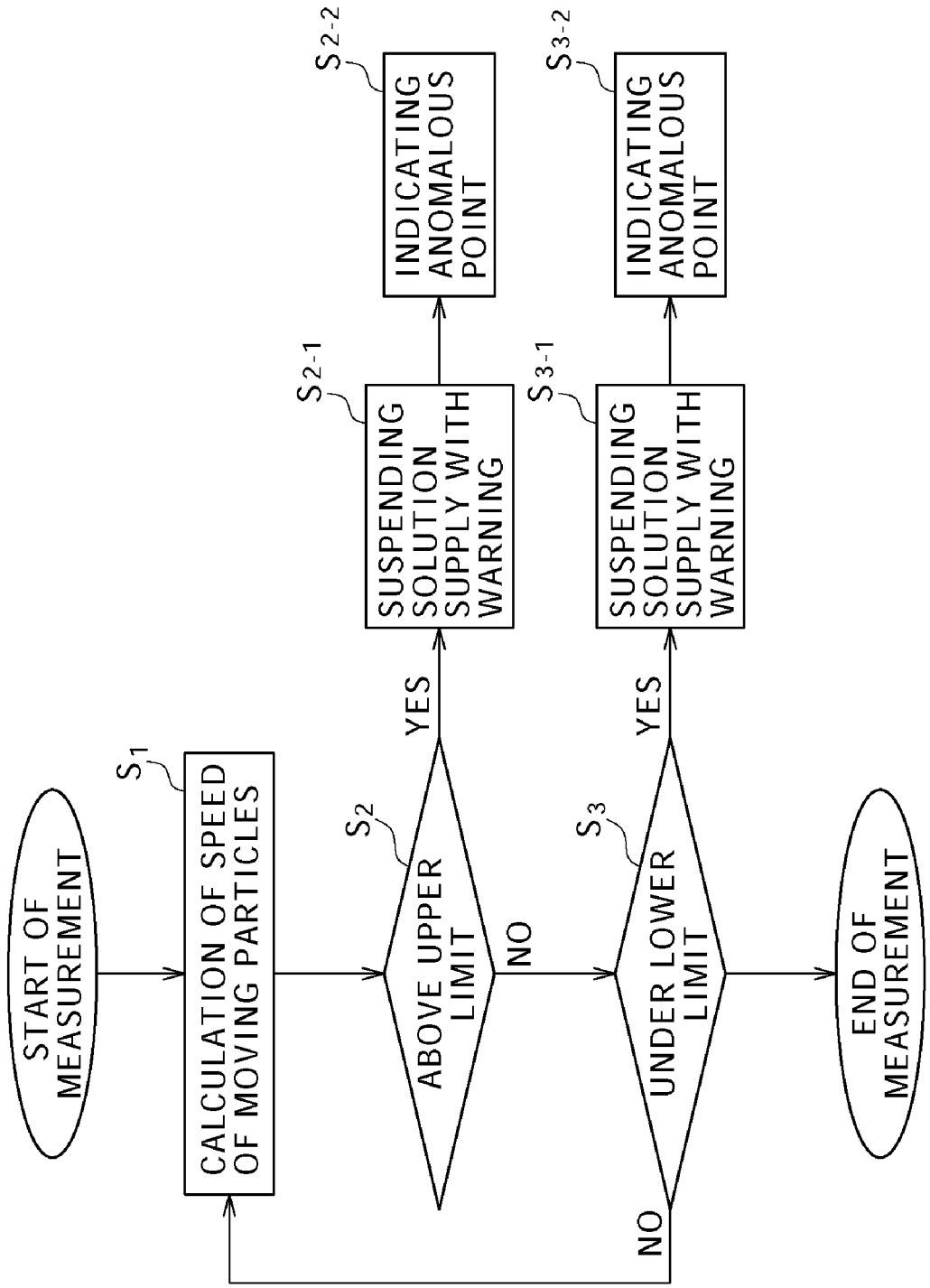
FIG. 3 is a flow chart illustrating the action of the microparticles measuring apparatus.

The action of the microparticles measuring apparatus A will be described below with reference to FIG. 3, which is a flow chart.

In Step S1 (which follows the start of measurement), the total control unit 3 calculates the speed of microparticles passing through the flow channel 11 by the procedure mentioned above according to the pulse width of the electrical signals sent from the optical detecting sections 21 and 22.

In Steps S2 and S3, the total control unit 3 determines whether or not the calculated speed is within the prescribed range. These steps may be carried out in any order or at the same time.

In Step S2, the total control unit 3 judges whether or not the calculated speed is over the prescribed range. If the result is YES, the flow of operation branches to Step S2-1, in which the total control unit 3 stops the action of the sample solution feeding section 41 and the sheath solution feeding section 42 so as to suspend the feeding of the sample solution and the sheath solution.

In the case where the speed of microparticles passing through the flow channel 11 is over the prescribed value, there is the possibility of the sample solution and sheath solution leaking from the flow channel 11 downstream the illuminating part S in the microchip 1, from the connection between the outlet 124 and the discharging section 43, or inside the discharging section 43. So, the total control unit 3 causes the image displaying unit 5 to display a warning about the solution leakage, thereby providing information to the operator.

When the total control unit 3 receives the detected values of the flow rate of the sample solution and sheath solution from the sensors 413, 423, and 433, Step S2-1 is followed by Step S2-2, in which the total control unit 3 causes the image displaying unit 5 to display the sensor which has detected the flow rate exceeding the prescribed range, thereby providing information to the operator. To be specific, this instance suggests that the flow rate has decreased due to leakage anywhere between the illuminating part S and the discharging section 43 and hence the sensor 433 has detected an "anomalous value" or the flow rate lower than the prescribed limit. Thus the image displaying unit 5 displays the sensor 433 as a possible point of leakage.

On the other hand, if the result in Step S2 is NO (or the total control unit 3 judges that the calculated value is not over the prescribed limit), the flow of operation continues to Step S3, in which the total control unit 3 judges whether or not the calculated value is under the prescribed limit. If the result is YES, the flow of operation branches to Step S3-1, in which the total control unit 3 stops the action of the sample solution feeding section 41 and the sheath solution feeding section 42 so as to suspend the feeding of the sample solution and the sheath solution.

An instance in which the flow rate of microparticles in the flow channel 11 is under the prescribed limit suggests the possibility of the sample solution or sheath solution leaking from the flow channel 11 upstream the illuminating part S of the microchip 1, from the connection between the sample solution inlet 121 and the sample solution feeding section 41, from the connection between the sheath solution inlet 122 and the sheath solution feeding section 42, or from the sample solution feeding section 41 or the sheath solution feeding section 42. It also suggests the possibility of the flow channel clogging anywhere in the apparatus. In such an instance, the total control unit 3 causes the image displaying unit 5 to display a warning of solution leakage or channel clogging, thereby providing information to the operator.

In addition, when the total control unit 3 receives the detected values of the flow rate of the sample solution and sheath solution from the sensors 413, 423, and 433, Step S3-1 is followed by Step S3-2, in which the total control unit 3 causes the image displaying unit 5 to display the sensor which has detected the flow rate exceeding the prescribed range, thereby providing information to the operator. To be specific, this instance suggests that the flow rate has decreased due to leakage in the sample solution feeding section 41 or anywhere between the sheath solution feeding section 42 and the illuminating part S and hence the sensor 413 or 423 has detected an anomalous value. Thus the image displaying unit 5 displays the sensor 413 or 423 as a possible point of leakage.

This case may be due to another probable reason that clogging has occurred anywhere in the apparatus and one or more of the sensors 413, 423, and 433 have detected the anomalous value according to the point of clogging. For example, if clogging occurs at the connection between the sample solution inlet 121 and the sample solution feeding section 41, the sensor 413 detects the anomalous value. Thus the image displaying unit 5 displays the sensor 413 as a possible point of clogging.

Figure 4:
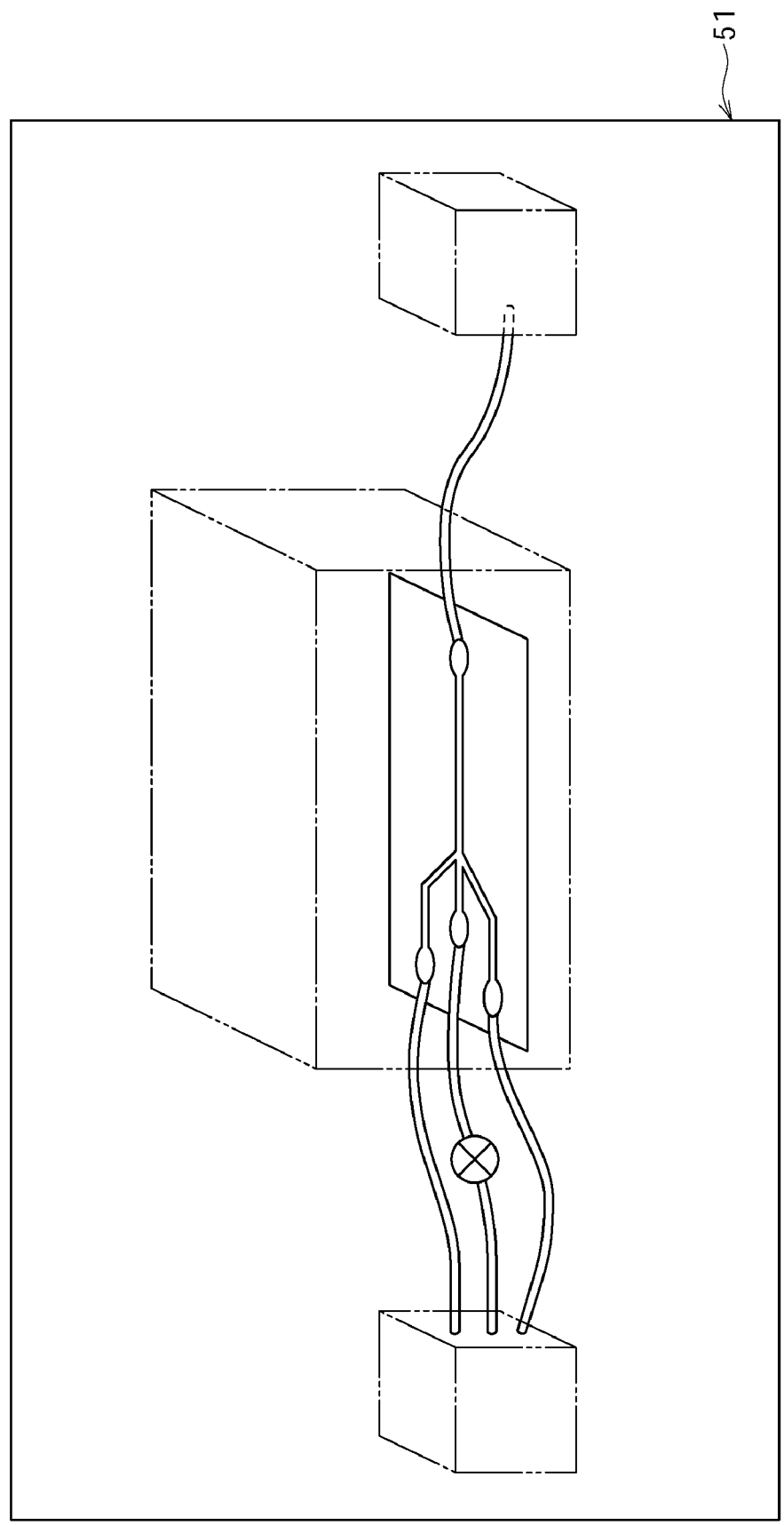
FIG. 4 is a schematic diagram illustrating one example of the image that is displayed on the image displaying unit.

FIG. 4 is a schematic diagram illustrating one example of the image 51 that is displayed on the image displaying unit 5 when the sensor 413 detects an anomalous value. The image 51 represents a simplified structure of the microparticles measuring apparatus A; it marks the point where leakage or clogging has occurred in the line provided with the sensor 413. The displayed mark permits the operator to identify the point where any anomaly has occurred, so that the operator may perform maintenance work, such as replacement of the microchip or the connecting parts thereof.

If the result in Step S3 is NO (or the calculated value is not over the lower limit of the prescribed range), the total control unit 3 returns to Step S1 to recalculate the speed of microparticles passing through the flow channel 11 and repeats the foregoing judging steps until measurement is completed.

The total control unit 3 may previously store and hold the values of the upper and lower limits of the speed to be used as the reference of judgment in Steps S2 and S3. Such values should be determined by repeated measurement of flow rate at which leakage or clogging does or does not occur.

The values of the upper limit or lower limit may also be established from the average value or median value (plus or minus a certain value) of the flow rate which has been obtained for several microparticles after the start of measurement. If a large fluctuation in the flow rate is observed during measurement, the feeding of the sample solution and the sheath solution should be suspended by the sample solution feeding section 41 and the sheath solution feeding section 42.

As mentioned above, the microparticles measuring apparatus A calculates the speed of microparticles passing through the flow channel 11 in response to electrical signals obtained by conversion from light emanating from the microparticles, and it suspends the feeding of microparticles when their speed exceeds the prescribed range, so that it detects the leakage of the sample solution and sheath solution or detects the clogging of the flow channel and automatically stops the feeding of the solution. In addition, the microparticles measuring apparatus A has a simple configuration because it does not need sensors to be arranged around the microchip.

Although the flow rate of microparticles passing through the flow channel 11 is easily affected even by a slight leakage of the sample solution or sheath solution, the microparticles measuring apparatus A is able to sensitively detect any leakage of the sample solution and sheath solution based on the speed of microparticles passing through the flow channel 11, thereby preventing accidents from occurring due to troubles in the apparatus or bursting of parts in the apparatus.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microparticles measuring apparatus comprising:
   optical detecting means for:
   (a) directing a laser beam toward microparticles passing through a flow channel,
   (b) detecting light emanating from the microparticles, and
   (c) converting the detected light into electrical signals; and
   controlling means for:
   (a) calculating a speed of the microparticles passing through the flow channel according to the electrical signals based on the speed being inversely proportional to pulse widths of said electrical signals,
   (b) determining if the calculated speed exceeds a prescribed limit or is lower than the prescribed limit; and
   (c) when the calculated speed exceeds the prescribed limit or is lower than the prescribed limit, suspending the supply of solution containing the microparticles.

2. The microparticles measuring apparatus as defined in claim 1, further comprising:
   the flow channel being formed on a microchip;
   supplying means for introducing into said flow channel a sample solution containing at least one of the microparticles and a sheath solution; and
   discharging means for discharging said sample solution and said sheath solution from said flow channel.

3. The microparticles measuring apparatus as defined in claim 2, wherein said supplying means and said discharging means are equipped with a sensor to detect the flow rate of at least one of the sample solution and the sheath solution.

4. The microparticles measuring apparatus as defined in claim 3, further comprising image displaying means for displaying said sensor which has detected the flow rate exceeding or being lower than the prescribed limit.

5. The microparticles measuring apparatus as defined in claim 4, which suspends the action of said supplying means when the speed of microparticle passing through said flow channel exceeds or is lower than the prescribed limit and displays any one of said sensors which has detected the flow rate exceeding or being lower than the prescribed limit on said image displaying means.

6. A microparticles measuring apparatus comprising:
   an optical detecting section configured to:
   (a) direct a laser beam toward microparticles passing through a flow channel,
   (b) detect light emanating from the microparticles, and
   (c) convert the detected light into electrical signals; and
   a controlling unit configured to:
   (a) calculate the speed of the microparticles passing through the flow channel according to the electrical signals based on the speed being inversely proportional to pulse widths of said electrical signals,
   (b) determine if the calculated speed exceeds a prescribed limit or is lower than the prescribed limit, and
   (c) when the calculated speed exceeds the prescribed limit or is lower than the prescribed limit, suspend the supply of solution containing the microparticles.

* * * * *